US 6,920,791 B2

(12) United States Patent
Wagner et al.

(10) Patent No.: US 6,920,791 B2
(45) Date of Patent: Jul. 26, 2005

(54) ULTRASOUND MONITORING OF OVERLAPPING WELDED JOINTS BETWEEN SHEETS

(75) Inventors: Joachim Wagner, Frechen (DE); Peter Wollny, Mettmann (DE)

(73) Assignee: GE Inspection Technologies Systems (DE)

( * ) Notice: Subject to any disclaimer, the term of this patent is extended or adjusted under 35 U.S.C. 154(b) by 41 days.

(21) Appl. No.: 10/450,433

(22) PCT Filed: May 12, 2001

(86) PCT No.: PCT/DE01/01822

§ 371 (c)(1),
(2), (4) Date: Jun. 13, 2003

(87) PCT Pub. No.: WO02/48704

PCT Pub. Date: Jun. 20, 2002

(65) Prior Publication Data

US 2004/0045358 A1 Mar. 11, 2004

(30) Foreign Application Priority Data

Dec. 15, 2000 (DE) .......................... 100 62 722

(51) Int. Cl.$^7$ .......................... G01N 29/06; G01N 29/26
(52) U.S. Cl. .............................. 73/620; 73/634; 73/635; 73/642
(58) Field of Search .......................... 73/588, 597, 598, 73/618, 620, 622, 624, 627, 628, 632, 633, 634, 635, 639, 641, 642, 644

(56) References Cited

U.S. PATENT DOCUMENTS

| | | | | |
|---|---|---|---|---|
| 3,628,375 A | * | 12/1971 | Pagano | 73/639 |
| 4,112,775 A | * | 9/1978 | Sylvester et al. | 73/627 |
| 4,174,636 A | | 11/1979 | Pagano | 73/636 |
| 4,217,782 A | * | 8/1980 | Pont | 73/637 |
| 5,920,014 A | * | 7/1999 | Waschkies | 73/597 |
| 6,178,819 B1 | * | 1/2001 | Smartt et al. | 73/622 |
| 6,250,163 B1 | * | 6/2001 | MacLauchlan et al. | 73/643 |
| 6,365,873 B1 | * | 4/2002 | Smartt et al. | 219/130.01 |

FOREIGN PATENT DOCUMENTS

| | | |
|---|---|---|
| DE | 195 12 176 A1 | 3/1996 |
| JP | 8184583 A | 7/1996 |

* cited by examiner

*Primary Examiner*—Hezron Williams
*Assistant Examiner*—Rose M. Miller
(74) *Attorney, Agent, or Firm*—Akerman Senterfitt

(57) ABSTRACT

In a method and a device for the ultrasonic monitoring of overlapping welded joints between a first sheet and a second sheet pulses are irradiated at an angle of between 15 and 80° into the first sheet by a first rotating probe head. The rotating probe head is arranged on a mount and has a tire rotating about the axle, coupled to the ultrasound transmitter and rolling along the first sheet, parallel to the overlapping welded joint. On ultrasound investigation of the overlapping welded joint the impulses transmitted to the second sheet are received by a second receiving rotating probe head, of similar construction to the first rotating probe head.

10 Claims, 2 Drawing Sheets

Figure 1:
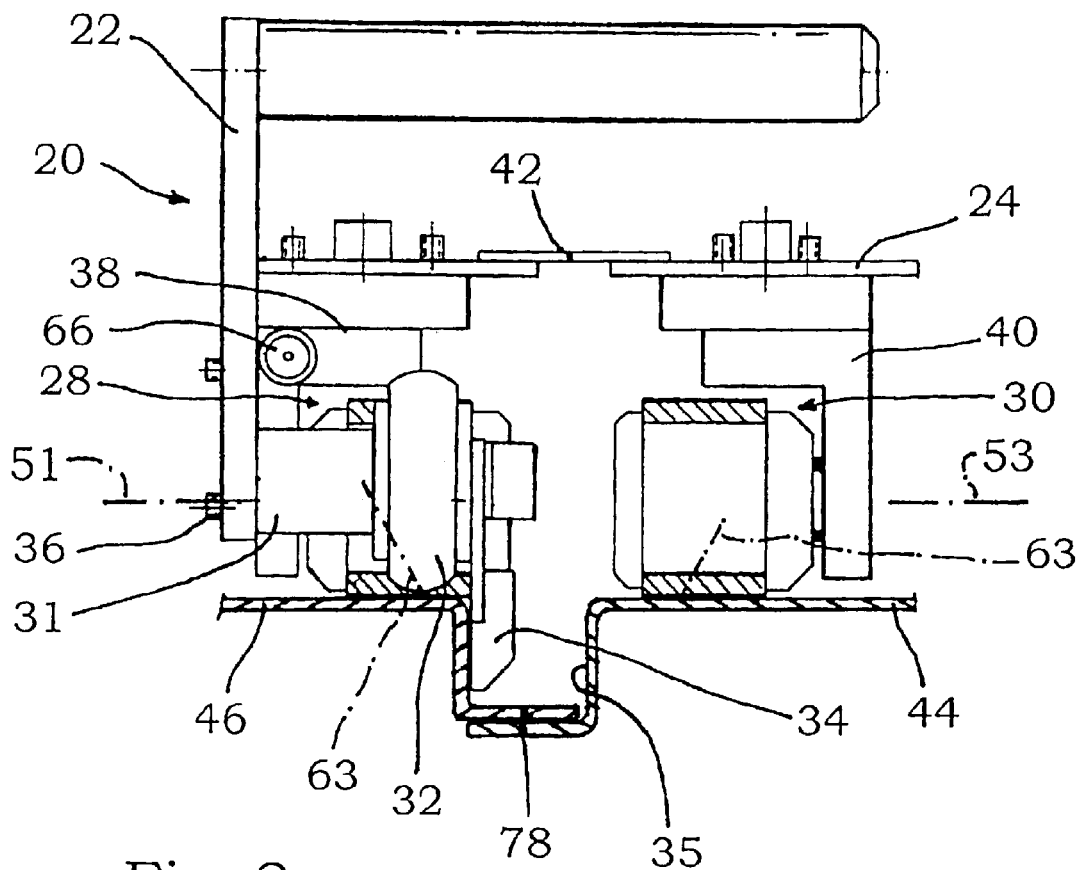

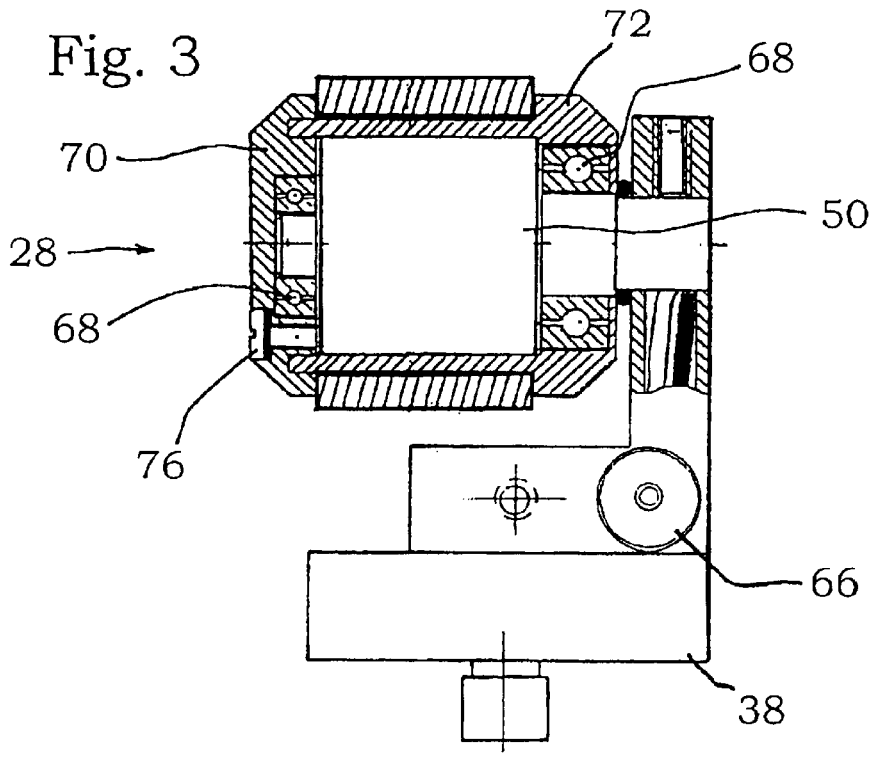
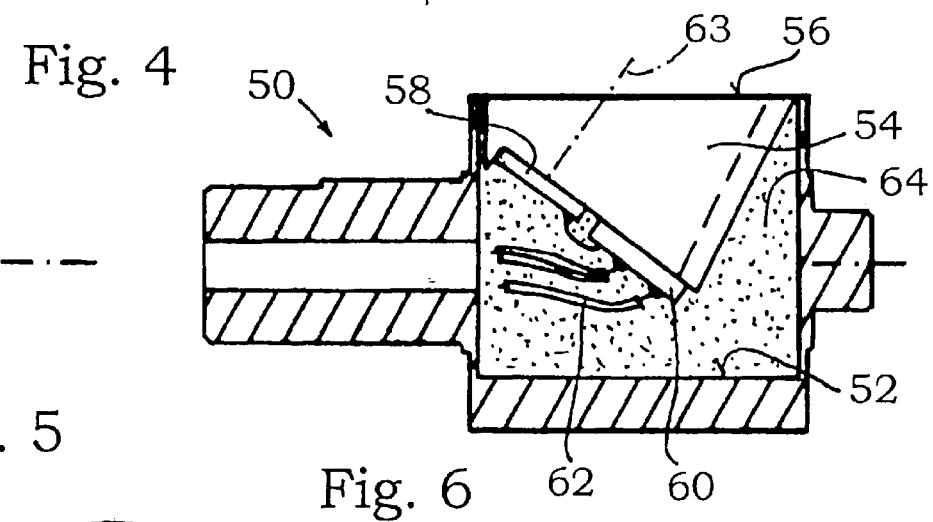
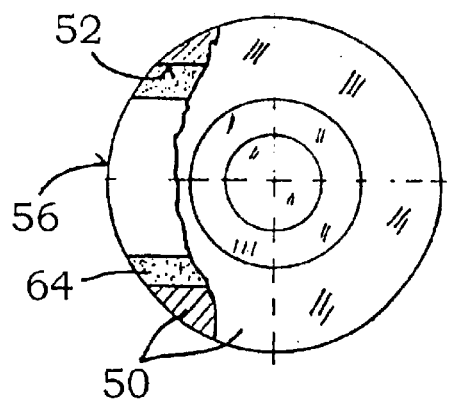
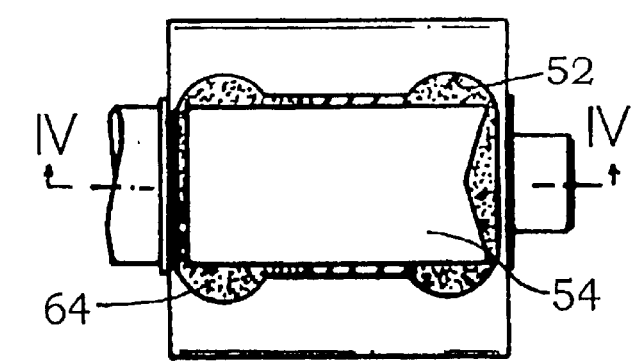

ULTRASOUND MONITORING OF OVERLAPPING WELDED JOINTS BETWEEN SHEETS

The invention relates to a method for the ultrasonic inspection of lap welds between a first metal sheet and a second metal sheet and to a device suitable for carrying the method into effect.

A plurality of methods and devices are known for testing welds in metal sheets, the reader is referred to the German book J. Krautkrämer & K. Krautkrämer "Werkstoffprüfung mit Ultraschall" ("Material Inspection with Ultrasounds"), $4^{th}$ edition. For the ultrasonic inspection of welds between a first and a second metal sheet by using the pulse method it is known therefrom to couple a first angle beam probe to the first metal sheet so that a transverse wave is created in the first metal sheet, which transverse wave propagates through the weld and is received, on the other side of the weld and, as a result thereof, on the second metal sheet, by an angle beam probe built substantially according to the same principle. Accordingly, ultrasonic transmission or transit is used. The degree of ultrasonic transmission is indicative of the configuration and the quality of the weld. Devices for such inspections are already known in which the two angle beam probes are mounted to a frame so that the probes need not be moved individually.

The shortcoming of the prior art methods and devices however is the coupling. Said coupling is performed by means of a coupling fluid, such as water. Such a coupling fluid necessarily wets the two metal sheets. Not only must the coupling fluid be removed from the metal sheets, but it must also be collected. A fluid coupling agent cannot always be utilized for testing metal sheets that are joined together by means of a lap weld or it may even happen that the processing plant rejects the use thereof. Inasmuch it is often difficult to convince a processing factory to perform ultrasonic inspection.

In the automotive industry, it is very important that the bond between two metal sheets intended to be joined be sufficient, since the quality and safety of the vehicle is determined by the configuration of the various welds. However, the following problem arises here. Prior to enamelling, the metal sheets that have been joined together by welding must be tested if one wants to have a chance at all to submit a weld to a rework process. But the metal sheets are not allowed to be affected, and more specifically to get dirty, from the inspection, which would involve the need for extensive rework to be done prior to enamelling, and would more specifically result in the fact that the enamel bond in the zones that have been scanned by a probe and contacted with a coupling agent would not be as good as at other locations on the metal sheet.

This is where the invention comes in. It is an object thereof to improve and develop the prior art methods and devices for the inspection of welds between two metal sheets, more specifically the inspection of lap welds between two metal sheets, in such a manner that even smaller welds, more specifically laser welds, can be reliably sensed, that a fluid coupling agent may be dispensed with and that it is made certain that the contact between probe and sheet will not affect subsequent enamelling or any other surface treatment.

With respect to the method, this object is achieved by a method for the ultrasonic inspection of lap welds between a first metal sheet and a second metal sheet which involves the following method steps emitting pulses at an angle ranging between 15 degree and 80.degree relative to a surface of the first metal sheet and generating a transverse wave in the first metal sheet by means of a first wheel probe which a) is mounted to a frame, which b) has an axle body that can not be rotated relative to the frame, said axle body defining a first axial line which is oriented substantially parallel to the surface of the first metal sheet, which c) is provided with an ultrasonic transducer fastened to the axle body and which d) has a tire that can be rotated about the axle body, is coupled to the ultrasonic transducer and rolls over the first metal sheet parallel to the lap weld, effecting through transmission on the lap weld using the pulses and receiving the pulses that have propagated through the lap weld into the second metal sheet using a receiving second wheel probe which a) is mounted to the frame, which b) has an axle body that can not be rotated relative to the frame, said axle body defining an axial line which is oriented substantially parallel to the surface of the second metal sheet, which c) is provided with an ultrasonic transducer fastened to the axle body and which d) has a tire that can be rotated about the axle body, is coupled to the ultrasonic transducer and rolls over the second metal sheet parallel to the lap weld, and evaluating the pulses received.

With respect to the device, this object is achieved by a device for the ultrasonic inspection of lap welds between a first and a second metal sheet using the pulse method, said device having a frame a first wheel probe which a) is provided with an axle body that is non-rotatably held on the frame, that b) has an ultrasonic transducer which has a main beam and is disposed in a recess of the axle body, the main beam thereof being oriented at an angle ranging between 15 and 80 degree relative to the axial line and that c) has a tire which is located outside of the ultrasonic transducer on the axle body and which is traversed by the main beam and a second wheel probe which a) is provided with an axle body that is non-rotatably held on the frame and is comprised of a recess, that b) has an ultrasonic transducer which has a main beam and is disposed in said recess in such a manner that the main beam thereof is oriented at an angle of from 15 to 80 degree relative to the axial line and that c) has a tire which is located outside of the ultrasonic transducer on the second axle body and which is traversed by the main beam.

The wheel probes permit to achieve a dry coupling to the metal sheets. A fluid coupling agent may thus be dispensed with. In selecting a suited material for the tires such as polyurethane or a soft grade rubber one achieves that the surfaces of the metal sheets are hardly affected at the places where they come into contact with the wheel probe; however that may be, the wheel rolling thereon does not leave any trace that would impair subsequent after treatment such as enamelling or a surface finishing treatment.

The invention permits to inspect welds in the roof region of motor vehicle bodyworks in particular, e.g., in proximity of a rain gutter. The gutter thereby permits to guide the frame to which the wheel probes are mounted.

It is important to always achieve the same conditions for the entry and for the exit of the ultrasound pulses. This is achieved by providing, as far as possible, uniform and linear contact of the two wheels over the entire length of the inspection path. The frame is designed accordingly and permits constant contact of the wheels over the inspection path.

Although wheel probes are well known in the art, they are configured as a standard vehicle tire that is filled with water instead of with compressed air. The spacing between a crystal and the area of engagement of the wheel into the surface of the metal sheet is strongly dependent on the pressure with which the wheel probe is pressed onto the metal sheet. Accordingly, the amplitude of the pulse entering the sheet is also strongly dependent on the respective one of the situations with the water-filled wheel probe. This is a disadvantage with through transmission in particular because the receiving probe is not capable of distinguishing between a variation in the amplitude of the entry pulse and an attenuation in the amplitude of the pulse as it propagates through the weld.

The invention permits to maintain a constant spacing between the crystal and the surface of the metal sheet over virtually the entire inspection path. For this purpose there is provided, i.a., that the tire have the same tire thickness allover. Thanks to the constant conditions for sound emission and the corresponding conditions on the receiving side, the invention permits to indeed substantially sense the weld. This makes it possible to inspect fine welds, like for example laser welds, as well.

In a preferred embodiment, each tire has a rim that is rotatably mounted to the corresponding axle body with a fluid-tight space being formed within said rim. In this way, the ultrasound crystal or ultrasonic transducer 58, which does not rotate, transmits the ultrasound pulse through a thin fluid layer consisting of a coupling fluid into the rim and into the tire. The motion of rotation takes place between the rim and the ultrasound crystal or rather the lead body thereof.

In a preferred development, at least one of the axle bodies is adjustably and/or elastically mounted to the frame. The associated wheel probe can thus adjust to the surface condition of the metal sheet, or rather, it can be adjusted accordingly.

In still another development, at least one guide roller is provided that rolls along one of the two metal sheets. As the two wheel probes 28, 30 lie substantially on one axial line, the angular position of the frame is undetermined. The guide roller dictates the angular position of the frame relative to the metal sheets. With two guide rollers, the position of the frame relative to the metal sheets is given by the guide rollers alone so that, as a result thereof, the contact pressure of the wheel probes is kept constant.

In the preferred embodiment, the two ultrasound transducers are built according to the same principle. They preferably have a frequency in excess of 1 MHz, more specifically in excess of 2 MHz. A frequency of 4 MHz is considered advantageous. At this frequency, even small defects in the welds can be detected.

The frame preferably has a guide shoe that is adapted to abut on a projection of one of the two metal sheets, said projection being oriented parallel to the lap weld. This provision facilitates the orientation of the frame while it is being moved over the weld.

In a preferred development, a mass is located between each axle body and the associated ultrasound crystal, said mass attenuating to the greatest possible extent the sonic coupling of the ultrasound crystal to the axle body. The pulse of the ultrasound crystal, which is radiated inward, is attenuated in this way. Further, the ultrasound crystal is positioned together with its lead body. Finally, the pulses of the ultrasound crystal are prevented from entering into the axle body.

In a preferred embodiment, each ultrasound crystal is mounted to a wedge-shaped lead body with a cylindrical surface area that coincides with the orientation of the cylinder jacket defining the associated axle body. In this way, transmission onto the rotating rim is facilitated and a constant gap between axle body, its component parts included, and the rim is achieved.

Figure 2:
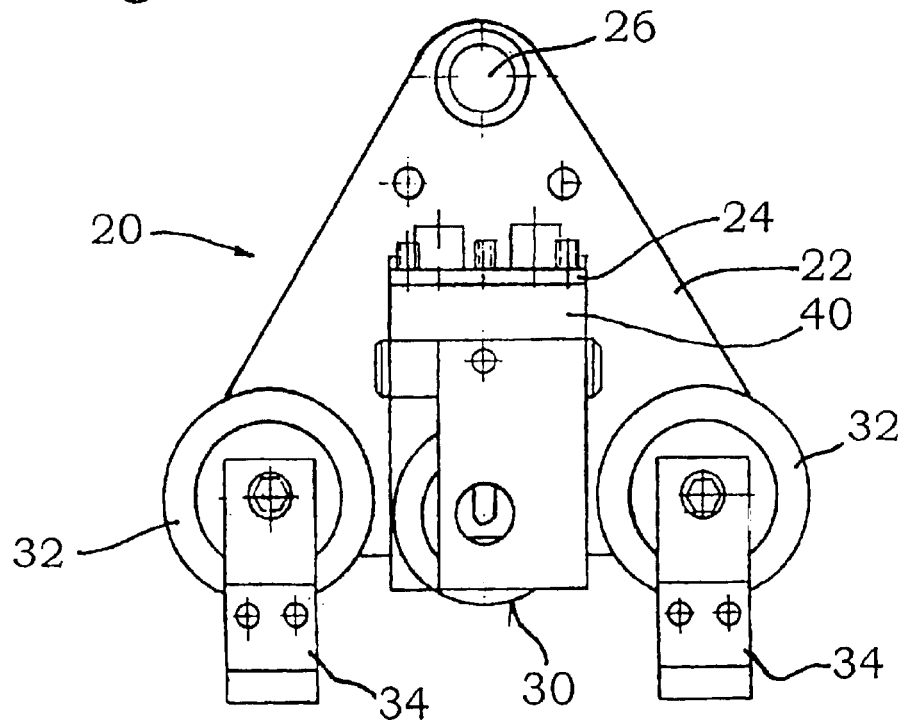

Further advantages and characteristics of the invention will become more apparent upon reading the other claims and the following non restrictive description of an embodiment thereof, given by way of example only with reference to the drawing, and serving to explain the method in accordance with the invention. In the drawing:

FIG. 1 is a side view of a device for the ultrasonic inspection as viewed in the direction of a weld joining two metal sheets, FIG. 2 is a front view of the device according to FIG. 1, FIG. 3 is a sectional view through a wheel probe, FIG. 4 is a sectional view through an axle body taken along the line IV—IV of FIG. 5 with the crystal and lead body of a wheel probe according to FIG. 3 being mounted thereto, FIG. 5 is a partially sectional view taken in the axial direction of the assembly according to FIG. 4 and FIG. 6 is a top view of the assembly according to FIG. 4.

The frame shown in the FIGS. 1 and 2 substantially consists of a main body, frame or mount 22 in the form of a triangular plate and of a supporting beam 24 oriented transversely relative thereto. A grab handle extending toward the supporting beam 24 is fastened to the main body 22. The supporting beam 24 protrudes approximately from the center of the main body 22 and serves to hold two wheel probes 28, 30. In proximity to the lower apexes of the triangle, axle journals 31 project from the main body 22, one guide roller 32 being rotatably carried by a respective one of said axle journals. A guide shoe 34 is fastened to the free end of a respective one of said axle journals 31, projects downward and engages for example into a rain gutter 35 of a roof of a motor vehicle bodywork. The guide rollers 32 and the guide shoes 34 are adjustable independent of each other, they are more specifically at least height adjustable. The guide shoes 34 can also be replaceable. From FIG. 1 it can be seen that, for varying the height of the guide rollers 32, a fastening screw 36 engages off center into the axle journal 31. The height of the guide roller 32 can be adjusted by releasing the fastening screw 36 and rotating the axle journal 31. Alternatively, a longitudinal slot may also be provided in the main body 22 for fastening the axle journal 31.

Two holding devices 38, 40 for the wheel probes 28, 30 are mounted to the supporting beam 24, the supporting beam has a leaf spring 42 located between them. They make it possible for the outer holding device 40 to move within a certain range relative to the inner holding device 38. As an alternative, a gimbal suspension could also be provided for the wheel probe 30, the outer one in FIG. 1. The objective to be achieved is that the two wheel probes each have a best possible contact with the metal sheets 44, 46 to be inspected. If the two holding devices 38, 40 would provide for a rigid hold, the wheel probes 28, 30 would not be capable of conforming to the deviations from an ideal plane in the metal sheets 44, 46.

The holding devices 38, 40 are more specifically adjustable in at least one direction in space, preferably in all three spatial directions, so that the associated wheel probes 28, 30 can be adjusted to optimally contact the metal sheets 44, 46 to be inspected. It is not necessary to adjust the first holding device 38 if the second holding device 40 is adjustable in all the three spatial directions.

The structure of the individual wheel probes 28, 30 will now be discussed. The two wheel probes 28, 30 are built according to the same principle. The first wheel probe 28 only will be described herein after. As the second wheel probe 30 is built according to the same principle as the first one, all of the explanations given also apply to the second probe, except for the fact that the adjective "first" needs to be replaced by "second".

As shown in the FIGS. 3 and 4, each of the wheel probes has an axle body 50 that is fixed by its end portion, the right one in the Figs., to the associated holding device, 38 in this case. Accordingly, the axle body 50 is non-rotatably connected to the holding device and, as a result thereof, to the main body 22. The axle body 50 of the wheel probe 28 defines a first axial line 51 that is oriented parallel to the metal sheet 44. In the same way, the axle body 50 of wheel probe 30 defines a second axial line 53 that is oriented parallel to the second metal sheet 46.

As more specifically shown in the FIGS. 4 and 6, the axle body 50 has a quite large recess 52. It is substantially shaped like a cube that is set back radially inward from a surface area and extends over almost the entire diameter of the central cylinder portion of the axle body 50.

A substantially wedge-shaped lead body 54 is located in the recess 52. It is conformed and machined in such a manner that the surface area 56 thereof, which is visible from outside, is flush with the cylinder jacket defining the axle body 50. This can be surveyed from FIG. 5. A first ultrasound crystal 58 is glued to a coupling surface of the lead body 54. The wedge angle of the lead body 54 is of approximately 37.degree. A solder terminal 60 is glued next to the first ultrasound crystal 38 on the same surface of the lead body 54, the first ultrasound crystal 58 and the connecting lines 62 being connected thereto. The first ultrasound crystal 58 is a composite crystal with a frequency of 4 MHz. It is in the shape of a circular disk which is 5 mm in diameter. The main beam thereof is indicated at 63.

The lead body 54 has a V-shaped groove that is shown in dashed line in FIG. 4. Said groove prevents standing waves from being created in the lead body 54. The lead body is made from acrylic.

The lead body 54 with the ultrasound crystal 58 and the other parts is embedded in the recess 52 by means of a mass 64. Said mass has good absorbing properties and prevents the ultrasound crystal 58 from being coupled to the axle body 50. More specifically, the rearward sent pulse of the ultrasound crystal 58 is intended to be attenuated and to have no effect as a result thereof. The mass 64 can be cast and solidifies later. It preferably consists of a plastic material that is blended with smaller components such as metal particles in a known manner. The connecting lines 62 are also embedded in the mass 64. They are threaded through a central hole and a window so that they can be run in a hollow inner space of the holding device 38 prior to being led to a plug in connection 66.

As can best be seen from FIG. 5, the surface of mass 64 is defined in such a manner that it lies on the cylinder jacket of the axle body 50. Seen from the outside, the axle body 50 with its filled recess 52 is therefore, as far as possible, an ideal cylinder.

To the left and to the right of the axle body 50 main region, in which the recess 52 is provided, there are concentric connection pieces of the axle body 50 to which ball bearings 68 are mounted. A cage is in turn rotatably mounted to said bearings, said cage being formed by an end cap 70 made from acrylic and by a rather cup-shaped surrounding part 72 made from acrylic. It forms a rim and is sealed to the outside so as to form an inner fluid tight chamber. The surrounding part 72 is in very close neighborhood of the main region of the axle body 50, a narrow tubular gap is left. The radial dimension thereof is small and does not exceed 1 mm for example. Said gap and the rest of the inner space are filled with a coupling fluid such as glycerine. It can be introduced at the site of a fill screw 76.

A tire 80 is disposed on the rim; it is in the shape of a tube portion and is made from a soft, rubber-like material. More specifically suited is polyurethane, natural or artificial rubber. The Shore hardness ranges between 10 and 40, preferably between 25 and 30. The material is similar to an eraser. It is important that the tire 80 has a constant thickness over the entire circumference thereof.

In practical operation, the emitting wheel probe 28 transmits at least one ultrasound pulse, usually a sequence of ultrasound pulses, into the first metal sheet 44. Due to the emission angle, transverse waves are created in the first metal sheet. These waves propagate through a weld 78 between the two metal sheets 44, 46. If the weld is in satisfactory condition, the pulses propagate through the weld 58 and enter the second metal sheet 46. There, they are received in the same manner as they were sent. Evaluation is carried out according to prior art. An instrument of the series USD, e.g., USD 16, of the applicant can be used.

It is possible to utilize the emitting wheel probe 28 as a receiving one and to operate the receiving wheel probe 30 as an emitter. The functions can be switched during operation as well.

What is claimed is:

1. A method for the ultrasonic inspection of lap welds between a first metal sheet and a second metal sheet, said method comprising the steps of:

applying a first wheel probe to a surface of the first metal sheet, emitting ultrasonic pulses at an angle ranging between 15 degrees and 80 degrees relative to the surface of the first metal sheet and generating a transverse wave in the first metal sheet;

allowing the ultrasonic pulses to pass through the lap weld;

applying a second wheel probe to a surface of the second metal sheet and receiving the ultrasonic pulses that have propagated through the lap weld into the second metal sheet;

providing a frame for carrying the first wheel probe and the second wheel probe;

wherein the first wheel probe comprises in combination a first axle body that is non-rotatable relative to said frame, said first axle body defining a first axial line which is oriented substantially parallel to the surface of the first metal sheet, a first ultrasonic transducer fastened to the first axle body, and a first tire that is rotatable about the first axle body, wherein said first tire is coupled to the first ultrasonic transducer, is dry-coupled to the first metal sheet and rolls over the first metal sheet parallel to the lap weld;

wherein said second wheel probe comprises in combination a second axle body that is non-rotatable relative to said frame, said second axle body defining a second axial line which is oriented substantially parallel to the surface of the second metal sheet, a second ultrasonic transducer fastened to the second axle body and a second tire that is rotatable about the second axle body, wherein said second tire is elastically mounted to the frame, is coupled to the second ultrasonic transducer, is dry-coupled to the second metal sheet and rolls over the second metal sheet parallel to the lap; weld; and evaluating the pulses received.

2. A device for the ultrasonic inspection of lap welds between a first metal sheet and a second metal sheet using the ultrasonic pulse method, said device having:
- a frame;
- a first wheel probe comprising in combination a first axle body that is non-rotatably held on the frame and which first axle body has a recess, said first axle body defining a first axial line, a first ultrasonic transducer disposed in the first recess of the first axle body and emitting pulses along a first main beam, the first main beam being oriented at an angle ranging between 15 and 80 degrees relative to the first axial line and a first tire rotating around the first axial line and being located outside of the first ultrasonic transducer on the first axle body, the first tire being traversed by the first main beam; and
- a second wheel probe comprising in combination a second axle body that is non-rotatably held on the frame and which second axle body has a second recess, said second axle body defining a second axial line, a second ultrasonic transducer disposed in-the second recess of the second axle body and receiving ultrasonic pulses along a second main beam, the second main beam being oriented at an angle ranging between 15 and 80 degrees relative to the second axial line, and a second tire which is elastically mounted to the frame, is located outside of the second ultrasonic transducer on the second axle body and which second tire is traversed by the second main beam.

3. The device of claim 2, wherein the tires each have a rim that is rotatably carried on the associated axle body and wherein a fluid tight space is formed within the rim.

4. The device of claim 2, wherein at least one guide roller is provided on the frame, said guide roller rolling over one of the two metal sheets.

5. The device of claim 2, wherein the ultrasonic transducers of the first wheel probe and the second wheel probe are built according to the same construction principle.

6. The device of claim 2, wherein the ultrasonic transducers of the two wheel probes have a frequency in excess of 1 MHz.

7. The device of claim 2, wherein a mass is provided between each axle body and the associated ultrasonic transducer, said mass attenuating to the greatest possible extent the ultrasonic coupling of the ultrasonic transducer to the axle body.

8. The device of claim 2, wherein each ultrasonic transducer is mounted to a wedge-shaped body, the main beam traversing said body, and wherein said body has a cylindrical surface area that coincides with the orientation of a cylinder jacket defining the associated axle body.

9. A device for the ultrasonic inspection of lap welds between a first metal sheet and a second metal sheet using the ultrasonic pulse method, said device having;
- a frame;
- a first wheel probe comprising in combination a first axle body that is non-rotatably held on the frame and which first axle body has a recess, said first axle body defining a first axial line, a first ultrasonic transducer disposed in the first recess of the first axle body and emitting pulses along a first main beam, the first main beam being oriented at an angle ranging between 15 and 80 degrees relative to the first axial line and a first tire rotating around the first axial line and being located outside of the first ultrasonic transducer on the first axle body, the first tire being traversed by the first main beam; and
- a second wheel probe comprising in combination a second axle body that is non-rotatably held on the frame and which second axle body has a second recess, said second axle body defining a second axial line, a second ultrasonic transducer disposed in-the second recess of the second axle body and receiving ultrasonic pulses along a second main beam, the second main beam being oriented at an angle ranging between 15 and 80 degrees relative to the second axial line, and a second tire which is located outside of the second ultrasonic transducer on the second axle body and which second tire is traversed by the second main beam.
- wherein the frame has a guide shoe that may be placed against a projection of one of the two metal sheets that is oriented parallel relative to the lap weld.

10. A device for the ultrasonic inspection of lap welds between a first metal sheet and a second metal sheet using the pulse method, said device having:
- a frame;
- a first wheel probe which
  - a) is provided an axle body that is non-rotatably held on the frame and has a recess,
  - b) has an ultrasound crystal which has a main beam and is disposed in a recess of the axle body, the main beam thereof being oriented at an angle ranging between 15 and 81 degrees relative to the firm axial line, and
  - c) has a tire which is located outside of the ultrasound crystal on the axle body and which is traversed by the main beam; and
- a second wheel probe which
  - a) is provided with an axle body with a second axial line that is non-rotatably held on the frame and is comprised of a recess,
  - b) has an ultrasound crystal which has a main beam and is disposed in said recess in such a manner that the main beam thereof is oriented at an angle of from 15 to 80 degrees relative to the second axial line, and
  - c) has a tire which is located outside of the ultrasound crystal on the axle body and which is traversed by the main beam,
- wherein each ultrasound crystal is mounted to a wedge-shaped body, the main beam traversing said body.

* * * * *